United States Patent [19]

Voges et al.

[11] 4,036,883
[45] July 19, 1977

[54] MANUFACTURE OF ISOMER-FREE 3-METHYLBUTYLAMINE

[75] Inventors: Dieter Voges, Mannheim; Siegfried Winderl, Heidelberg-Wieblingen; Herbert Mueller, Frankenthal, all of Germany

[73] Assignee: BASF Aktiengesellschaft, Ludwigshafen (Rhine), Germany

[21] Appl. No.: 634,232

[22] Filed: Nov. 21, 1975

[30] Foreign Application Priority Data

Nov. 27, 1974 Germany .............................. 2456006

[51] Int. Cl.$^2$ ..................... C07C 85/06; C07B 1/00
[52] U.S. Cl. ........................... 260/585 B; 260/690
[58] Field of Search .................................. 260/585 B

[56] References Cited

U.S. PATENT DOCUMENTS

| 3,022,349 | 2/1962 | Lemon et al. ............... 260/585 B |
| 3,278,598 | 10/1966 | Markiewitz ..................... 260/563 |
| 3,520,933 | 7/1970 | Adam et al. ................... 260/585 B |

FOREIGN PATENT DOCUMENTS 1,364,219   8/1974   United Kingdom ............ 260/585 B

OTHER PUBLICATIONS

Groggins, "Unit Processes in Organic Synthesis", Fifth Edition, pp. 574-576 (1958).
Jardine et al., "J. Chem. Soc., Org", vol. 4, pp. 458-462 (1966).

*Primary Examiner*—Daniel E. Wyman
*Assistant Examiner*—John J. Doll
*Attorney, Agent, or Firm*—Keil, Thompson & Shurtleff

[57] ABSTRACT

Manufacture of 3-methylbutylamine by reacting 2-methylbuten-1-ol-4 with hydrogen and a molar excess of ammonia simultaneously at about 140° to 240° C. at superatmospheric pressure in the presence of a hydrogenation catalyst metal or metals, i.e., the transition metals of Group VIII or copper.

4 Claims, No Drawings

MANUFACTURE OF ISOMER-FREE 3-METHYLBUTYLAMINE

It is known to prepare amines by aminolysis of alcohols with ammonia in contact with dehydrating or hydrogenating-dehydrogenating catalysts. The latter reaction is particularly preferred for the production of pure chemicals, hydrogen being present if necessary. The generally accepted theory is that the alcohol is dehydrogenated to the aldehyde in a first reaction stage and the aldehyde then reacts with ammonia to form the imine which is then hydrogenated by hydrogen to the amine.

In this way, 3-methylbutylamine-1 may be obtained from 3-methyl-butanol-1. It is used as an intermediate in the preparation of pharmaceuticals. The purity of the compounds is therefore particularly important.

3-methylbutanol (isoamyl alcohol) is available, for example, by hydroformylation of isobutene and hydrogenation. However, the alcohol thus obtained contains small portions of isomeric amyl alcohols which are virtually impossible to separate by ordinary industrial separating processes. The undesirable isomeric alcohols are derived either from impurities in the isobutene, for example cis- and trans-butene-2 and n-butene-1, or they are produced during hydroformylation of the isobutene, since the reaction takes place not only at the $\alpha$-carbon atom of the olefin but also, to a small extent, at the $\beta$-position. Thus the isoamyl alcohol available by oxo reaction is unsuitable for the manufacture of isomer-free 3-methylbutylamine, particularly as the separation of isomeric amylamines is just as impossible as that of the alcohols.

In a different process, it is possible to prepare isomer-free 3-methylbutylamine by reacting methallyl chloride with potassium cyanide and hydrogenating the resulting dimethyl acrylonitrile. However, this process is relatively expensive on account of the poor availability of the starting materials and is not environmentally acceptable on account of the quantities of salt which pass into the waste water.

It is an object of the present invention to prepare isomer-free 3-methylbutylamine-1 in an industrially simple manner. We have found that isomer-free 3-methylbutylamine-1 may be obtained by aminolysis of 3-methylbutanol obtained by thermal addition of formaldehyde to isobutene to form 2-methylbuten-1-ol-4 followed by hydrogenation of the unsaturated alcohol to form 3-methylbutanol.

On investigation of this hitherto unknown route it was found, surprisingly, that isomer-free 3-methylbutylamine could be advantageously prepared by direct reaction of the 2-methylbuten-1-ol-4, obtained from isobutylene and formaldehyde, with ammonia in contact with a hydrogenation catalyst at elevated temperature and at high yields, the success of this method being as good as or better than whens the unsaturated alcohol is first hydrogenated to the saturated alcohol followed by aminolysis thereof.

In general, the process of the invention is carried out in known manner in the presence of hydrogen and at appropriate elevated pressure.

This result was not foreseeable for a number of reasons and is contrary to all expectations:

1. It is well known that the aminolysis of the alcohol in contact with a hydrogenating/dehydrogenating catalyst produces, in a first reaction stage, the aldehyde. However, the 2-methylbuten-ol-4 expected as the intermediate rearranges spontaneously to dimethyl acrolein (see German Published Application No. 2,041,976); this $\alpha,\beta$-unsaturated carbonyl compound is thermally unstable and undergoes, at temperatures above 100° C, alkaline-catalyzed (ammonia) oligomerization and polymerization reactions which take place many times faster than the relatively slow aminolysis and hydrogenation. This well-known reaction behavior would lead one to expect not more than small, if any, yields of desired amine.

2. Hydrogenation-dehydrogenation catalysts such as are used in the present invention are transition metal catalysts which, at the (relatively high) reaction temperature, are capable of isomerizing 2-methylbuten-1-ol-4 to 2-methylbuten-2-ol-4, as described, for example, in German Published Application No. 1,901,709 or German Pat. No. 1,768,023. This alcohol also produces dimethyl acrolein on dehydrogenation and this would have again led one to expect side reactions.

3. Also, 2-methylbuten-1-ol-4 has the tendency to stabilize by allyl re-arrangement to dimethylvinylcarbinol (see German Published Application No. 1,793,265). The latter compound cannot be converted to the desired 3-methylbutylamine by aminolysis.

4. Finally, it was feared that ammonia would condense with the olefinic alcohol at its double bond under the drastic reaction conditions and on account of the catalytic action of the transition metals. As far as we know, virtually no aminolysis reactions have been attempted using alcohols having isolated double bonds.

Contrary to expectations, all of these side reactions are absent in the process of the invention.

The reaction of 2-methylbuten-1-ol-4 with ammonia to form 3-methylbutylamine-1 takes place under the action of the well-known catalysts based on transition metals in Group VIII of the Periodic Table or copper. These agents, which are normally used as hydrogenation catalysts, have a dehydrogenating and hydrogenating action (see above) when effecting replacement of the hydroxyl group by the amino group (aminolysis). Examples of suitable catalysts are those containing iron, cobalt, nickel, ruthenium, rhodium, platinum or copper or compounds thereof. Mixtures of these metals or metal compounds may also be used for the aminolysis, which mixtures may be further activated by additives.

Suitable additives are, for example, alkali metal and alkaline earth metal oxides, boric acid, phosphoric acid and compounds of elements in Groups I, II, IV, V, VI and VII of the Periodic Table.

Particularly suitable catalysts consist, for example, of cobalt, nickel and copper with or without additions of manganese and phosphoric acid. Another suitable catalyst may consist of cobalt, manganese and phosphoric acid, sintered cobalt (unsupported) or of nickel containing additions of copper and chromium. In most cases a support such as activated charcoal, pumice, silica gel, diatomaceous earth and, particularly advantageously, aluminum oxide is present, the portion of catalytically active metal being, for example, from 1 to 30% of the total weight of catalyst. Suitable recipes for the preparation of such catalysts are given, for example, in French Pat. No. 7,037,604, U.K. Pat. No. 1,225,875, U.S. Pat No. 3,128,311 and German Pat. No. 1,172,268. The U.S. Patent is incorporated herein by reference.

The catalysts are normally used in reduced (metallic) form. In other words, they are prepared, for example, by reduction of the metal oxides with hydrogen at temperatures between 80° and 500° C or, as in the case of Raney metal, are directly obtained in metallic form during preparation. Alternatively, they may be prepared by reducing the oxides or metal salts with other reducing agents, particularly metal alkyls or other metals.

The process of the invention is carried out by known industrial methods either batchwise or continuously using fixed-bed catalysts or suspended catalysts.

The reaction, i.e. both hydrogenation and the reaction with ammonia, requires temperatures of from about 140° to 240° C and residence times of from about 10 to 60 minutes.

The reaction with ammonia, considered in itself, may be carried out without the action of hydrogen, but it has been found advantageous to carry out this aminolysis under a hydrogen pressure of from 100 to 200 bars. This gives a suitable reaction rate. The process of the invention may also be carried out in water, an inert solvent such as tetrahydrofuran or in the reaction product itself.

In order to obtain the best yields of primary amine, the ammonia is used in excess and re-used in conventional manner. It is generally sufficient to use an excess of from 5 to 10 moles, although it is preferred to use a molar excess of ammonia of from 15 to 20, this giving yields of more than 80%, based on converted alcohol.

The reaction product may generally be highly purified in a simple manner, for example by distillation, giving a product which is suitable for pharmaceutical applications if desired.

EXAMPLE

A vertical high-pressure tube having a capacity of 500 parts by volume is filled with a catalyst containing 10% w/w of cobalt oxide, 10% w/w of nickel oxide and 4% w/w of copper oxide supported on aluminum oxide. After reducing the catalyst with hydrogen at 250° C, 50 parts per hour of 2-methylbuten-1-ol-4 and 350 parts by volume per hour of liquid ammonia are passed upwardly through the catalyst at a temperature of 210° C. Hydrogen is passed in to give a pressure of 270 atmospheres gauge. Ammonia is distilled off from the resulting reaction mixture. There are obtained 63 parts per hour of a mixture containing 85% of 3-methylbutylamine, calculated as being free from water by gas-chromatographic analysis. Distillation gives pure 3-methylbutylamine, the isomeric purity thereof being at least 99.5%, as determined by nuclear resonance.

We claim:

1. A process for manufacture of pure 3-methylbutylamine-1 which comprises reacting 2-methylbuten-1-ol-4 with hydrogen and a molar excess of ammonia simultaneously at about 140° to 240° C. at superatmospheric pressure in the presence of a hydrogenation catalyst containing one or more metals selected from the group consisting of iron, cobalt, nickel, ruthenium, rhodium, platinum and copper, distilling off the excess ammonia from the reaction mixture, and recovering pure 3-methylbutylamine-1.

2. A process as claimed in claim 1 wherein said catalyst is sintered, unsupported cobalt.

3. A process as claimed in claim 1 wherein said catalyst contains a mixture of metals selected from the group consisting of cobalt, nickel and copper; cobalt, nickel, copper, manganese and phosphoric acid; cobalt, manganese and phosphoric acid; and nickel, copper and chromium.

4. A process for the production of pure 3-methylbutylamine-1 which comprises reacting hydrogen and ammonia simultaneously with a hydroformylation reaction mixture derived by the thermal condensation of isobutene and aqueous formaldehyde, said reaction mixture consisting mainly of 2-methylbuten-1-ol-4 and containing minor amounts of isomeric alcohols derived from cis- and trans-butene-2 and n-butene-1 impurities in the isobutene reactant or from hydroformylation of the isobutene at the $\beta$-position, said simultaneous reaction of ammonia, hydrogen and said reaction mixture being carried out at about 140° to 240° C. in the presence of a catalyst containing a catalytically active amount of one or more metals from the group consisting of iron, nickel, cobalt, ruthenium, rhodium, platinum and copper.

* * * * *